(12) United States Patent
Duprieu et al.

(10) Patent No.: US 11,326,332 B2
(45) Date of Patent: May 10, 2022

(54) ADVANCED TOILET WITH REMOTE BIDET POD

(71) Applicants: Jean-Baptiste P. Duprieu, New York, NY (US); James Keith Vanderpant, New York, NY (US)

(72) Inventors: Jean-Baptiste P. Duprieu, New York, NY (US); James Keith Vanderpant, New York, NY (US)

(*) Notice: Subject to any disclaimer, the term of this patent is extended or adjusted under 35 U.S.C. 154(b) by 0 days.

(21) Appl. No.: 17/193,894

(22) Filed: Mar. 5, 2021

(65) Prior Publication Data

US 2021/0277643 A1  Sep. 9, 2021

Related U.S. Application Data

(60) Provisional application No. 62/986,220, filed on Mar. 6, 2020.

(51) Int. Cl.
| | |
|---|---|
| *E03D 9/08* | (2006.01) |
| *E03D 11/00* | (2006.01) |
| *A47K 13/24* | (2006.01) |
| *G06F 3/147* | (2006.01) |
| *A61B 5/00* | (2006.01) |
| *A61B 5/0205* | (2006.01) |

(52) U.S. Cl.
CPC .............. *E03D 9/08* (2013.01); *A47K 13/24* (2013.01); *E03D 11/00* (2013.01); *A61B 5/0205* (2013.01); *A61B 5/4872* (2013.01); *A61B 5/4875* (2013.01); *G06F 3/147* (2013.01)

(58) Field of Classification Search
CPC ....................................... E03D 9/08
USPC ........... 4/420.2, 447, 448, 420.3, 420.4, 420
See application file for complete search history.

(56) References Cited

U.S. PATENT DOCUMENTS

| | | | | |
|---|---|---|---|---|
| 4,237,560 | A * | 12/1980 | Riegelman | E03D 9/08 219/217 |
| 5,647,069 | A * | 7/1997 | Han | E03D 9/08 4/420.2 |
| 2006/0258915 | A1* | 11/2006 | Ueda | A47K 13/30 600/301 |
| 2007/0143909 | A1* | 6/2007 | Montgomery | E03D 9/10 4/213 |
| 2008/0141444 | A1* | 6/2008 | Lin | E03D 11/14 4/217 |
| 2010/0083430 | A1* | 4/2010 | Chen | A47K 13/305 4/237 |
| 2018/0163385 | A1* | 6/2018 | Chen | E03D 9/05 |
| 2018/0171614 | A1* | 6/2018 | Chen | E03D 9/08 |
| 2018/0235416 | A1* | 8/2018 | Poleki | A47K 13/302 |
| 2020/0337509 | A1* | 10/2020 | Ho | A47K 13/10 |
| 2021/0015314 | A1* | 1/2021 | Sylvia | E03D 9/08 |
| 2021/0207352 | A1* | 7/2021 | Kim | E03D 5/04 |

* cited by examiner

*Primary Examiner* — Lori L Baker
(74) *Attorney, Agent, or Firm* — Eric Hanscom

(57) ABSTRACT

An advanced toilet/bidet with a remote pod that stores both the majority of the bidet hardware and an advanced software program, providing a toilet seat that is thinner and lighter than a traditional toilet/bidet combination. The toilet seat has a bidet nozzle, and an internal cavity in which additional hardware and software is stored. The toilet seat has sensors the record health-related data on each user and has a unique cleaning mechanism to ensure the highest sanitary standards.

20 Claims, 5 Drawing Sheets

ADVANCED TOILET WITH REMOTE BIDET POD

CROSS REFERENCE TO RELATED APPLICATIONS

This application claims priority to U.S. Provisional Application No. 62/986,220, entitled Advanced Toilet with Remote Bidet and Related Software Application, with a filing date of Mar. 6, 2020.

STATEMENT REGARDING FEDERALLY SPONSORED RESEARCH OR DEVELOPMENT

This invention was not federally sponsored.

BACKGROUND OF THE INVENTION

Field of the Invention

This invention relates to the general field of toilets, and more specifically, to a special toilet seat with unique biometric sensors and a remote bidet pod housing mechanical and electronic components and a related software application that can be attached to a standard toilet, providing a safer, cleaner, and healthier experience than that afforded by the prior art. The toilet seat sensors detect and record a number of biometric observations and provide feedback to a user.

Brief Description of Invention

The invention comprises an external pod which houses the majority of the traditional bidet hardware and also houses a software program. The invention can be hooked into an existing toilet with a water tank, where the external pod controls the bidet function, and additionally comprises electrical connections and an advanced software system that runs the device.

There exist current toilet seats with bidets, but these toilet seats are generally large, heavy and bulky because of the extensive internal hardware needed to support both the toilet and bidet function. This creates a toilet seat that is expensive, and difficult to install/remove because of its size and weight. The current invention circumvents this problem by removing the majority of the hardware for the bidet and putting it in an attractive yet functional pod that sits to the side of the toilet. This allows for a much thinner toilet seat design that is traditionally found in All-in-one toilets with built-in bidets, and can be used with existing toilets.

The prior art has several examples of bidets built into toilets, and even some toilets with various software applications, both there are either a) too bulky, b) too inefficient, or c) too expensive. Thus, there has existed a long-felt need for an efficient toilet that combines light weight, a thin profile, and is capable of obtaining and processing health-related data to help the users keep track of their health.

The current invention provides just such a solution by providing an advanced toilet seat/bidet with a remote pod that stores both the bidet hardware and an advanced software program, providing a toilet seat that is thinner and lighter than a traditional toilet/bidet combination. The toilet seat has sensors that record health-related data on each user and has a unique cleaning mechanism to ensures the highest sanitary standards.

OBJECTS OF THE INVENTION

It is therefore an object of the present invention to provide a remote bidet function which can allow a standard toilet, that is thin and lightweight, to have a bidet function.

An additional object of the invention includes providing a remote pod that contains the hardware to run a bidet.

A final object of the invention is to provide a software program that collects data from sensors on the toilet seat and provides the user many health-related measurements.

There has thus been outlined, rather broadly, the more important features of the invention in order that the detailed description thereof may be better understood, and in order that the present contribution to the art may be better appreciated. There are additional features of the invention that will be described hereinafter and which will form the subject matter of the claims appended hereto. The features listed herein and other features, aspects and advantages of the present invention will become better understood with reference to the following description and appended claims. The accompanying drawings, which are incorporated in and constitute part of this specification, illustrate embodiments of the invention and, together with the description, serve to explain the principles of the invention.

It should be understood that while the preferred embodiments of the invention are described in some detail herein, the present disclosure is made by way of example only and that variations and changes thereto are possible without departing from the subject matter coming within the scope of the following claims, and a reasonable equivalency thereof, which claims I regard as my invention.

BRIEF DESCRIPTION OF THE FIGURES

One preferred form of the invention will now be described with reference to the accompanying drawings.

DETAILED DESCRIPTION OF THE FIGURES

Figure 1:
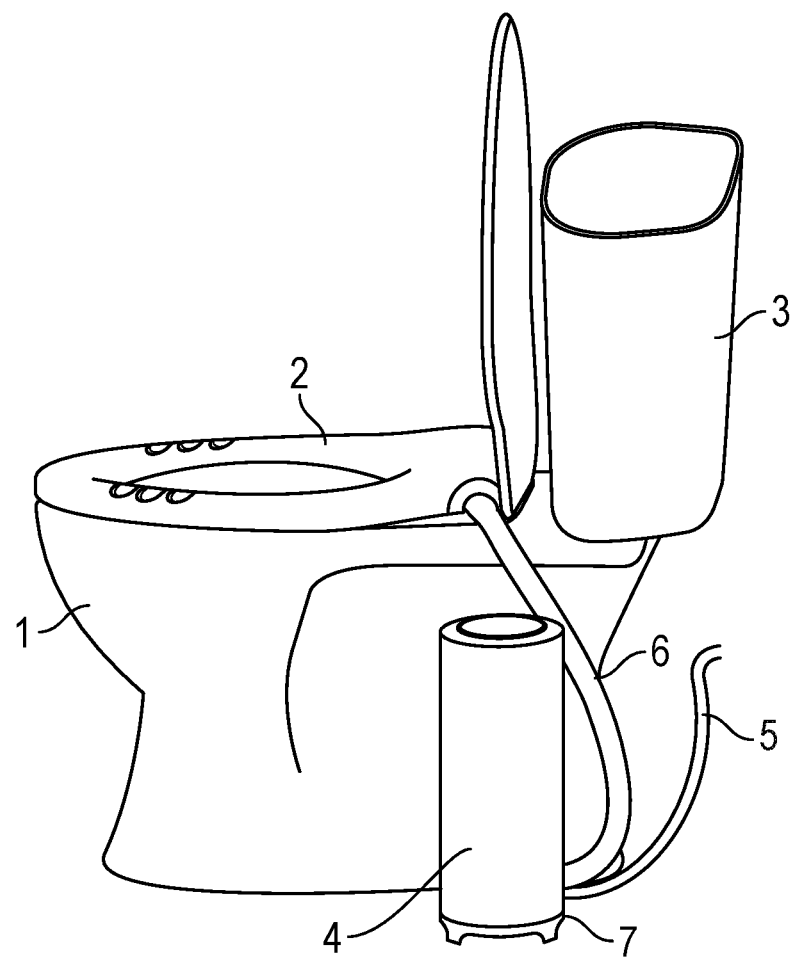
FIG. 1 is a side view of the invention.

Many aspects of the invention can be better understood with references made to the drawings below. The components in the drawings are not necessarily drawn to scale. Instead, emphasis is placed upon clearly illustrating the components of the present invention. Moreover, like reference numerals designate corresponding parts through the several views in the drawings. Before explaining at least one embodiment of the invention, it is to be understood that the embodiments of the invention are not limited in their application to the details of construction and to the arrangement of the components set forth in the following description or illustrated in the drawings. The embodiments of the invention are capable of being practiced and carried out in various ways. In addition, the phraseology and terminology employed herein are for the purpose of description and should not be regarded as limiting.

FIG. 1 is a side view of the invention. The toilet 1 has a toilet seat 2, into which sensors have been placed (not visible in this figure). A toilet tank 3 stores water and is connected to an external pod 4 by a wall to pod water hose 5. The pod 4, in turn, supplies water to the toilet bidet (not shown in this figure) through a pod to toilet water hose 6. The unit is powered by an electrical connection 7. By removing the hardware from a traditional toilet seat with a bidet, the invention provides a significantly lighter and thinner toilet, making it easier to install and remove.

Figure 2:
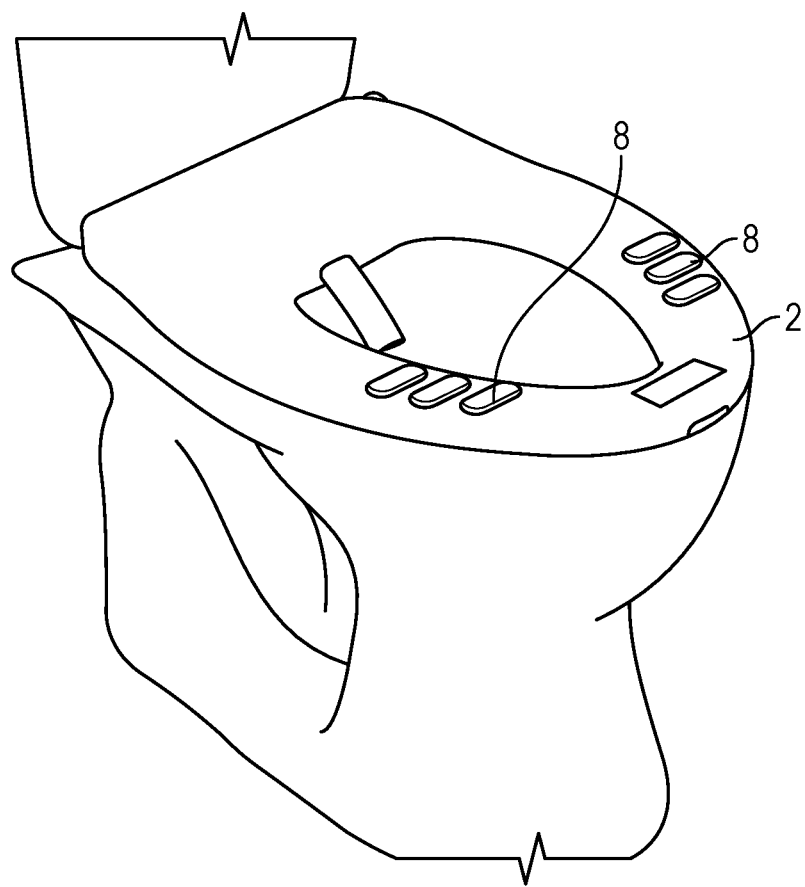
FIG. 2 is a perspective view of the toilet seat showing the location of the sensors.

FIG. 2 is a perspective view of the toilet seat 2 showing the location of the sensors 8. The toilet seat has sensor pads 8 in at least two locations that take biometric data from a person sitting on the toilet. The design of this toilet allows for touch-free opening and closing, a heated seat, bidet, a control for the water temperature, deodorizer, sound masking, self-cleaning function, user recognition, and utilization of the advanced software system that runs the unit. The biometric sensors take measurements every time a person sits down, including but not limited to hydration levels, heart rate/HRV/ECG, body weight, BMI, body fat, muscle mass, and frequency of use tracking.

Figure 3:
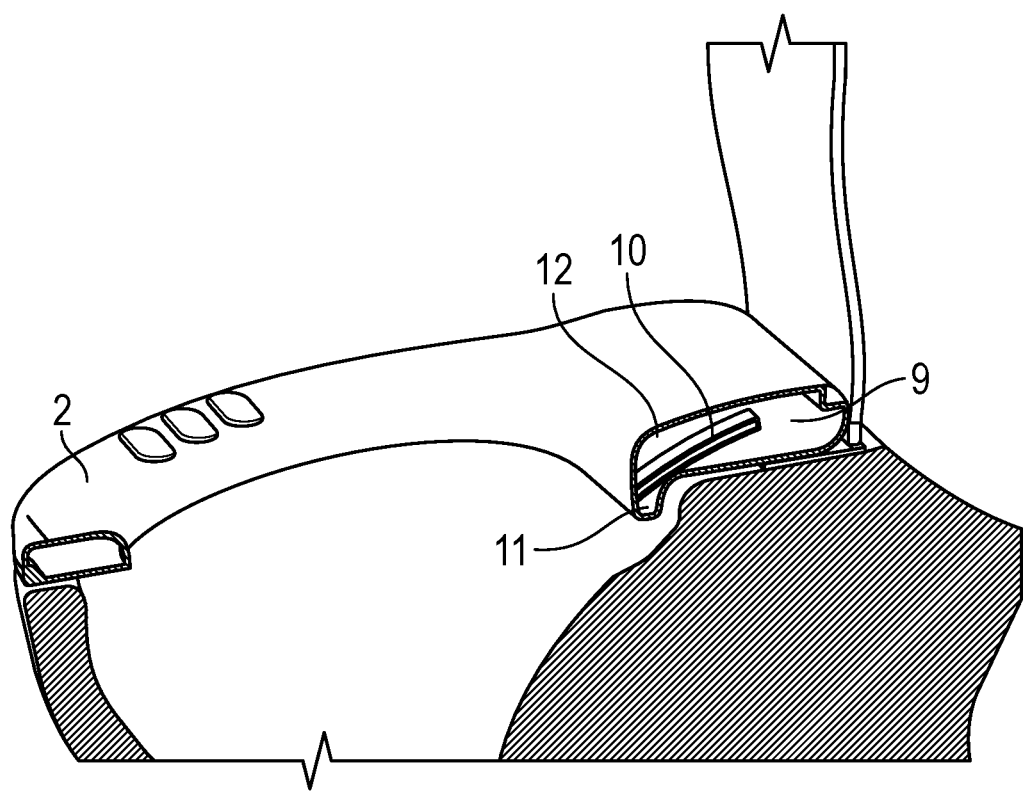
FIG. 3 is a cross-sectional view of the toilet seat.

FIG. 3 is a cross-sectional view of the toilet seat. The bidet water nozzle 10 is hidden inside of toilet seat in a nozzle cavity in the under hang 11 of the toilet. There are additional cavities, 9 and 12, to house additional hardware to sit inside of the toilet rather than outside.

Figure 4:
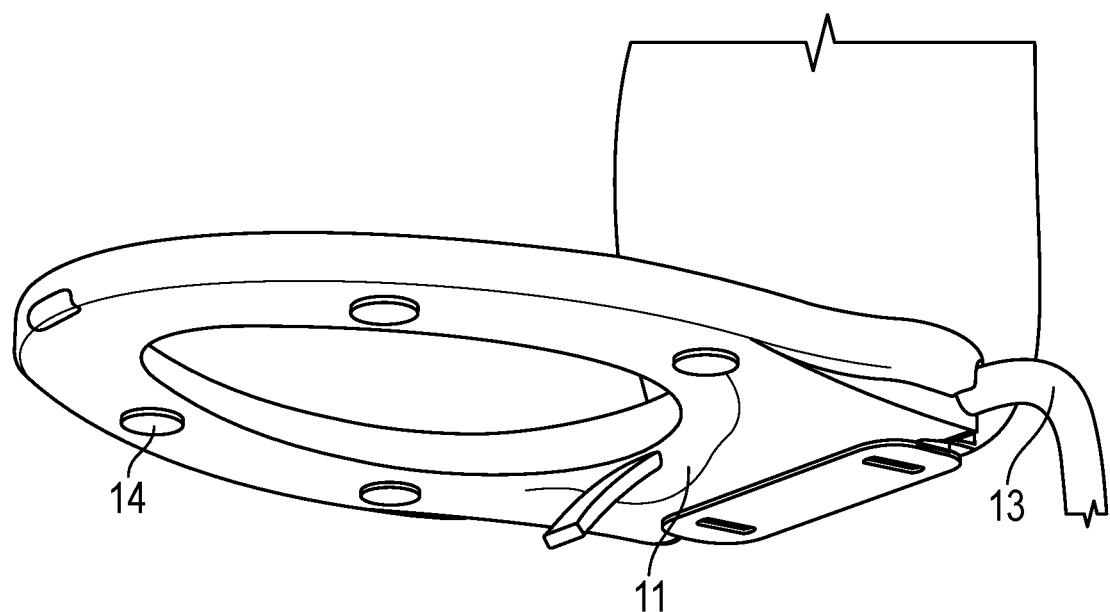
FIG. 4 is a bottom, perspective view of the toilet seat.

FIG. 4 is a bottom, perspective view of the toilet seat. This figure shows how the cleaning mechanism is stored in the actual seat ring, rather than in a base housing as is found in the prior art. The water supply 13 from the pod enters the assembly, and the inner cavities house all the hardware, leaving the under hang 11 clear from any electrical components. Silicon pads 14 help stability and also have scales/weight sensors to measure users' weight and weight distribution for user recognition.

Figure 5:
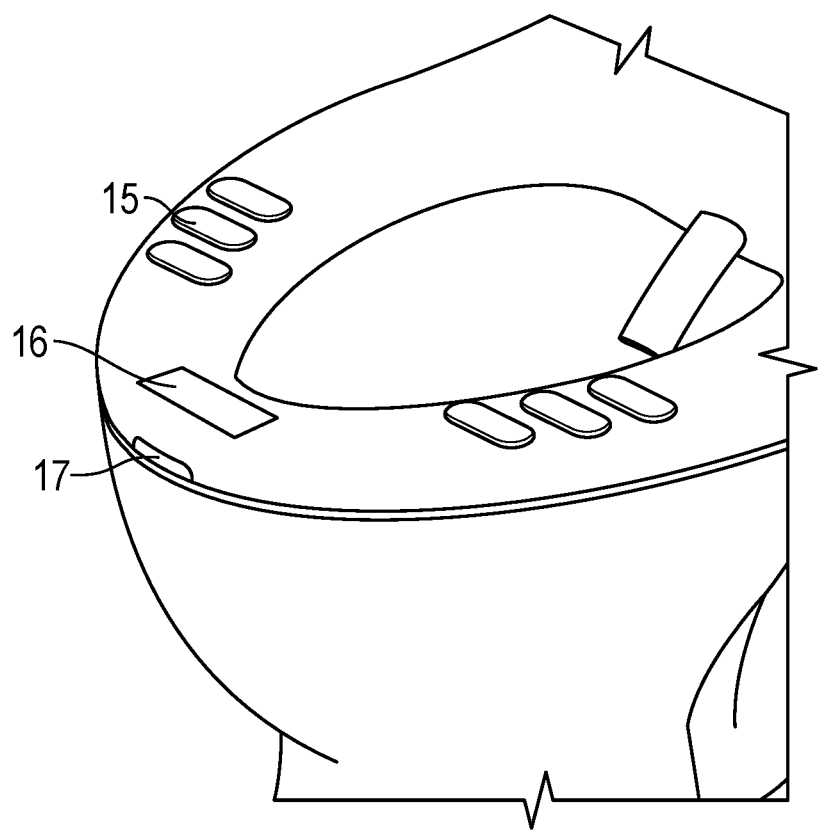
FIG. 5 is a perspective view of the toilet seat showing the sensor placement.

FIG. 5 is a perspective view of the toilet seat portion of the invention. The bottom of the seat can feature either matrix displays 16 or flexible, bendable OLED/LCD under the top surface of the seat with can be activated by the microcontroller. The seat also has Front Sensors 17 in the front of the seat to detect the user's presence. When the user is detected as approaching the seat the lid will automatically open. Also used to detect when no user is present for a certain amount of time and will automatically close.

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

REFERENCE NUMBERS USED

1. Toilet (generally)
2. Toilet Seat
3. Water tank
4. Pod (external)
5. Wall to Pod Water hose.
6. Pod to Toilet water hose. (+Electrical+deodorizer)
7. Electrical connection to wall
8. Sensors
9. Cavity for internal parts/motors/plumbing etc.
10. Water Nozzle
11. Under-hang
12. Cavity for Vacuum breaker valve
13. Water supply from pod and electrical+deodorizer spray (all in one pipe)
14. Silicon pads that help stability but also have scales/weight sensors to measure users' weight and weight distribution for user recognition.
15. Sensor pad surface that records the biometric information.
16. Dot matrix display hidden inside seat
17. Front Sensors in the front of the seat to detect the user's presence. When the user is detected as approaching the seat the lid will automatically open. Also used to detect when no user is present for a certain amount of time and will automatically close.

That which is claimed:

1. A toilet seat assembly, comprising a toilet seat, a pod, an electrical connection, a water-source-to-pod hose, and a pod-to-toilet hose, where the electrical connection provides power to the pod, where the water-source-to-pod hose connects a water source to the pod, where the pod-to-toilet hose connects the pod to the toilet seat, where the toilet seat comprises at least one sensor, where the pod houses both a hardware component and a software component, where the hardware component comprises a water heater, an Electrical Engineering-Mechanical control outline, a flow meter, a solenoid/regulator, a speaker, a ground connection for water, a drain, and a descale port, where the at least one sensor sends at least one data to the software component, where the software component performs at least one calculation and displays the at least one calculation on a viewing device, where the toilet seat comprises a cavity, where one or more internal parts are stored, where the cavity is not visible from outside of the toilet assembly, where the cavity houses a nozzle, where the nozzle is fed water from the pod-to-toilet hose, where the nozzle protrudes from an underside of the toilet seat, and delivers a stream of water, where the cavity additionally comprises a vacuum breaker valve, where the pod additionally comprises a deodorizer container, where the deodorizer container is connected to the pod-to-toilet hose, such that a quantify of deodorizer is added to the quantity of water moving from a bidet to the nozzle in the pod-to-toilet hose, where the toilet seat comprises one or more silicon pads, where each of the one or more silicon pads is located in a front, underside location on the toilet seat, where each of the one or more silicon pads have a scale and a weight distribution sensor such that each of the one or more silicon pads can measure a user's weight and determine how that user's weight is distributed in a weight distribution assessment, where the software component uses the user's weight and the weight distribution assessment to identify the user, where the toilet seat additionally comprise one or more sensor pads, where each of the one or more sensor pads is located in a top, front position on the toilet seat, where each of the one or more sensor pads records at least one item of biometric information, where the toilet seat comprises at least two sensors, where the at least two sensors are biosensors, where the toilet seat additionally comprises at least one dot matrix display, where each dot matrix display is located inside the toilet seat, where the toilet seat additionally comprises one or more front sensors, where each of the one or more front sensors is located on a front section of the toilet seat, where each of the one or more front sensors detects when a potential user approaches the toilet seat, and causes a toilet lid to automatically open, and, can also detect when there are no potential users in the vicinity and cause the toilet lid to automatically close after passage of a certain time period.

2. The toilet seat assembly of claim 1, where the software component comprises an initial detection phase, a phone detection phase, a sex-of-user detection phase, a collection of health data phase, a computation of health data phase, and a display of data, and additionally comprising a hand-held digital display device, where the hand-held digital display device has, at a minimum, a health function, a control function, a store function, and an account function.

3. A toilet seat assembly, comprising a toilet seat, a pod, an electrical connection, a water-source-to-pod hose, and a pod-to-toilet hose, where the electrical connection provides power to the pod, where the water-source-to-pod hose connects a water source to the pod, where the pod-to-toilet hose connects the pod to the toilet seat, where the pod is an external pod.

4. The toilet seat assembly of claim 3, where the toilet seat comprises at least one sensor.

5. The toilet seat assembly of claim 4, where the toilet seat additionally comprises an internal cavity, a water nozzle, an under-hang component, and a vacuum breaker.

6. The toilet seat assembly of claim 5, where the pod houses both a hardware component and a software component, where the hardware component comprises a water heater, an Electrical Engineering-Mechanical control outline, a flow meter, a solenoid/regulator, a speaker, a ground connection for water, a drain, a descale port, and a deodorizer bottle.

7. The toilet seat assembly of claim 6, where the bidet pod is an external pod and is attachable to an existing toilet.

8. The toilet seat assembly of claim 7, where the at least one sensor sends at least one data to the software component, where the software component performs at least one calculation and displays the at least one calculation on a viewing device.

9. The toilet seat assembly of claim 4, where the toilet seat comprises a cavity, where one or more internal parts are stored, where the cavity is not visible from outside of the toilet assembly.

10. The toilet seat assembly of claim 9, where the cavity houses a nozzle, where the nozzle is fed water from the pod-to-toilet hose, where the nozzle protrudes from an underside of the toilet seat and delivers a stream of water.

11. The toilet seat assembly of claim 10, where the cavity additionally comprises a vacuum breaker valve.

12. The toilet seat assembly of claim 11, where the pod additionally comprises a deodorizer container, where the deodorizer container is connected to the pod-to-toilet hose, such that a quantify of deodorizer is added to the quantity of water moving from the bidet to the nozzle in the pod-to-toilet hose.

13. The toilet seat assembly of claim 4, where the toilet seat comprises one or more silicon pads, where each of the one or more silicon pads is located in a front, underside location on the toilet seat, where each of the one or more silicon pads have a scale and a weight distribution sensor such that each of the one or more silicon pads can measure a user's weight and determine how that user's weight is distributed in a weight distribution assessment.

14. The toilet seat assembly of claim 13, where the software component uses the user's weight and the weight distribution assessment to identify the user.

15. The toilet seat assembly of claim 14, where the toilet seat additionally comprises one or more sensor pads, where each of the one or more sensor pads is located in a top, front position on the toilet seat, where each of the one or more sensor pads records at least one item of biometric information.

16. The toilet seat assembly of claim 15, where the toilet seat additionally comprises at least two sensors, where each of the at least two sensors are biosensors.

17. The toilet seat assembly of claim 4, where the toilet seat additionally comprises at least one dot matrix display.

18. The toilet seat assembly of claim 17, where each dot matrix display is located inside the toilet seat.

19. The toilet seat assembly of claim 4, where the toilet seat additionally comprises one or more front sensors, where each of the one or more front sensors is located on a front section of the toilet seat, where each of the one or more front sensors detects when a potential user approaches the toilet seat, and causes a toilet lid to automatically open, and, can also detect when there are no potential users in the vicinity and cause the toilet lid to automatically close after passage of a certain time period.

20. The toilet seat assembly of claim 19, where the software component comprises an initial detection phase, a phone detection phase, a sex-of-user detection phase, a collection of health data phase, a computation of health data phase, and a display of data, and additionally comprising a hand-held digital display device, where the hand-held digital display device has, at a minimum, a health function, a control function, a store function, and an account function.

* * * * *